United States Patent [19]

Devanathan et al.

[11] Patent Number: 5,773,789
[45] Date of Patent: Jun. 30, 1998

[54] METHOD OF MAKING AN ORTHOPAEDIC IMPLANT HAVING A POROUS METAL PAD

[75] Inventors: Deva Devanathan, Warsaw; Steve Krebs; Steve T. Lin, both of Fort Wayne; Clarence M. Panchison, Warsaw, all of Ind.; James J. Morr, Panama City Beach, Fla.

[73] Assignee: Bristol-Myers Squibb Company, New York, N.Y.

[21] Appl. No.: 652,193

[22] Filed: May 23, 1996

Related U.S. Application Data

[63] Continuation-in-part of Ser. No. 609,210, Mar. 1, 1996, Pat. No. 5,672,284, which is a continuation of Ser. No. 228,774, Apr. 18, 1994, Pat. No. 5,504,300.

[51] Int. Cl.$^6$ .................................................... B23K 26/00
[52] U.S. Cl. ...................................................... 219/121.64
[58] Field of Search .................. 219/121.63, 121.64, 219/121.72, 121.85

[56] References Cited

U.S. PATENT DOCUMENTS

| | | |
|---|---|---|
| 3,605,123 | 9/1971 | Hahn . |
| 3,855,638 | 12/1974 | Pilliar . |
| 4,536,894 | 8/1985 | Galante et al. ............................ 623/22 |
| 4,636,219 | 1/1987 | Pratt et al. ................................ 623/22 |
| 4,660,755 | 4/1987 | Farling et al. .......................... 228/178 |
| 4,693,721 | 9/1987 | Ducheyne ................................. 623/16 |
| 4,828,566 | 5/1989 | Griss ......................................... 623/23 |
| 4,835,357 | 5/1989 | Schalk .............................. 219/121.64 |
| 4,863,474 | 9/1989 | Brown et al. ............................. 623/16 |
| 4,969,904 | 11/1990 | Koch et al. ............................... 623/16 |
| 5,013,324 | 5/1991 | Zolman et al. ........................... 623/23 |
| 5,027,998 | 7/1991 | Bugle ..................................... 228/44.5 |
| 5,030,233 | 7/1991 | Ducheyne ................................. 623/16 |
| 5,057,108 | 10/1991 | Shetty et al. ............................. 606/53 |
| 5,080,674 | 1/1992 | Jacobs et al. ............................. 623/20 |
| 5,108,432 | 4/1992 | Gustavson ................................. 623/16 |
| 5,139,528 | 8/1992 | Koch et al. ................................ 623/66 |
| 5,171,148 | 12/1992 | Wasserman et al. .................... 433/215 |
| 5,198,308 | 3/1993 | Shetty et al. ............................. 428/608 |
| 5,242,706 | 9/1993 | Cotell et al. ................................ 427/2 |
| 5,245,155 | 9/1993 | Pratt et al. ........................ 219/121.63 |
| 5,397,359 | 3/1995 | Mittelmeier et al. ..................... 623/16 |

FOREIGN PATENT DOCUMENTS

| | | |
|---|---|---|
| 0 191 182 | 8/1986 | European Pat. Off. . |
| 0 273 871 | 7/1988 | European Pat. Off. . |
| 0 560 418 | 9/1993 | European Pat. Off. . |
| 0 599 426 | 6/1994 | European Pat. Off. . |
| 0 623 687 | 11/1994 | European Pat. Off. . |
| 64-2645 | 4/1989 | Japan . |

OTHER PUBLICATIONS

B. Bryan et al., "Welding Processes; current status, developments and future trends," *New Metallilc Materils and New Fabrication Processes,* 1987, pp. 3.1–3.36.

U. Dilthey and A. Risch, "Laser Welding of Stainless Steels and Stainless/low–alloy Material Combinations."

Metzbower et al., "Depth of Penetration in Laser Beam Welding," *Laser Materials Processing,* 1994, pp. 203–212.

P. Khan and A. Paul, "Experimental and Theoretical Evaluation of Mass Transport During Laser Welding," *International Conference on Beam Processing of Advanced Materials,* 1992, pp. 217–227.

Bagdasarov et al., "1 kW Processing YAG Laser," *Paton Welding Journal* 1991, pp. 310–312.

(List continued on next page.)

*Primary Examiner*—Geoffrey S. Evans
*Attorney, Agent, or Firm*—Todd A. Dawson

[57] ABSTRACT

An orthopaedic implant body is formed which has a supporting surface. A porous metal pad is formed to fit the supporting surface of the body. The porous metal pad is clamped and/or adhesively bonded to the supporting surface. A laser beam is coupled between the porous metal pad and the implant body at a plurality of locations so as to form a coalescence of metal between the porous metal pad and the body.

24 Claims, 2 Drawing Sheets

OTHER PUBLICATIONS

Balbi et al., "Laser Repairing Techniques for Superalloy Components," *Metallurgical Science and Technology,* 1992, pp. 56–64.

Matsuda et al., "Solidification Crace Susceptibility of Laser Weld Metal in 0.2C–Ni–Cr–Mo steels: Effects of Bead Configuration and S and P Contents," *Welding International,* 1993, pp. 686–692.

Z. Sun and T. Moisio, "A Comparative Study of Dissimilar Metal Welding Using Various Processes," *International Trends in Welding Science and Technology,* 1993, pp. 433–438.

Von W. Dick and E. Morscher, "Experiences With the Development of Non–cemented Prostheses," *Medizinische–Orthopadische Technik,* 1986, pp. 6–10.

Ignatiev, et al., "The High Speed Pyrometer System for Laser Welding, Cutting, Heat Treatment and Alloying Processes Temperature Control," *Laser Treatment of Materials Processing ECLAT,* 1992, pp. 15–20.

Sun et al., "Weld Metal/ferritic Steel Interface in Laser Welded Austenitic/ferritic Dissimilar Steel Joints," *Journal of Materials Science Letters 13,* 1994, pp. 802–805.

Zheng Sun, "Residual Stress in Laser Welded Dissimilar Steel Tube–to–Tube Joints," *Scripta Mettalurgica et Materialia,* 1993, pp. 633–637.

J.M. Pettetier and M. Robin, "Metal–ceramic Joining by Laser," *Journal De Physique IV,* 1993, pp. 1061–1064.

A. Paul and P. Khan, "Mass Transport During Laser Welding of Stainless Steels and Alloys Used by U.S. Navy," *Journal of Laser Applications,* 1994, pp. 32–37.

Bob Irving, "Laser Beam and GMA Welding Lines Go On–Stream at Arvin Industries," *Welding Journal,* 1993, pp. 47–50.

C.J. Dawes, "Materials," *Laser Welding—A Pracical Guide,* 1992, pp. 51–77.

METHOD OF MAKING AN ORTHOPAEDIC IMPLANT HAVING A POROUS METAL PAD

CROSS REFERENCE TO RELATED APPLICATIONS

This is a continuation-in-part of U.S. patent application Ser. No. 08/609,210, filed Mar. 1, 1996, entitled "ORTHOPAEDIC IMPLANT AND METHOD OF MAKING SAME", now U.S. Pat. No. 5,672,284, which is a continuation of U.S. patent application Ser. No. 08/228,774, filed Apr. 18, 1994, entitled "ORTHOPAEDIC IMPLANT AND METHOD OF MAKING SAME", now U.S. Pat. No. 5,504,300.

BACKGROUND OF THE INVENTION

1. Field of the Invention

The present invention relates to orthopaedic implants, and, more particularly, to orthopaedic implants having a porous metal pad attached thereto.

2. Description of the Related Art

Orthopaedic implants, such as knee or hip implants, may include one or more porous surfaces at the exterior thereof. The porous surfaces enhance implant fixation within the bone by allowing bony ingrowth therein or penetration of bone cement. The porous surface is typically in the form of a pad constructed of fiber metal, metal beads or a wire mesh. The fibers, beads or wires are typically interconnected with each other using a sintering or diffusion bonding process. The porous metal pad is cut to shape to fit a supporting surface formed on the orthopaedic implant body.

One known method of attaching the porous metal pad to the implant body is to clamp the porous metal pad against the supporting surface of the implant body, and thereafter metallurgically bond the porous metal pad to the implant body using a diffusion bonding or sintering process. A problem with sintering the porous metal pad to the implant body is that this process is both time consuming and expensive from a manufacturing standpoint. For example, during sintering, the ramp up and cool down time for a sintering furnace is approximately 14 hours per cycle. If the porous metal pad is being connected, e.g., to the interior bone engaging surface of a femoral knee component, it may take a minimum of three cycles to complete the sintering operation. The complex geometric interior design of the femoral knee component may require that only one or two porous metal pads be attached to the femoral knee component during one cycle of the sintering process. The typical interior of the femoral knee component defines five distinct surfaces which require connection with a porous metal pad. Therefore, to completely bond the porous metal pad to the interior of the femoral knee component may require in excess of 42 hours of furnace time. Added to this is the time required to connect the clamping tool to the implant for holding the porous metal pad in contact with the supporting surface of the implant. It is thus apparent that providing a porous metal pad on an implant using a sintering process is relatively time consuming and expensive.

It is also known to diffusion bond a fiber metal pad to a thin metal foil, which in turn is attached to an orthopaedic implant body using a laser welding process. For details of such an attachment process, reference is hereby made to U.S. patent application Ser. No. 08/609,210, entitled "ORTHOPAEDIC IMPLANT AND METHOD OF MAKING SAME," which is assigned to the assignee of the present invention and incorporated herein by reference. In general, a porous metal pad, such as a fiber metal pad, is diffusion bonded to a thin metal foil. The fiber metal pad and thin metal foil are each configured to be received within a recess formed in the orthopaedic implant body. The edges of the thin metal foil extend to the exterior of the recess formed in the orthopaedic implant body. A laser welder is used to weld the thin metal foil to the orthopaedic implant body, and thereby indirectly attach the fiber metal pad to the implant body.

What is needed in the art is a method of attaching a porous metal pad to an orthopaedic implant body wherein the porous metal pad is attached to the implant body at locations other than the periphery of the porous metal pad.

What is further needed in the art is a method of attaching a porous metal pad to an implant body which is faster than a sintering process.

SUMMARY OF THE INVENTION

The present invention provides a method of attaching a porous metal pad to a body of an orthopaedic implant by coupling a laser beam between the porous metal pad and the body at a plurality of predetermined locations.

The invention comprises, in one form thereof, a method of making an orthopaedic implant. An orthopaedic implant body is formed which has a supporting surface. A porous metal pad is formed to fit the supporting surface of the body. The porous metal pad is clamped and/or adhesively bonded to the supporting surface. A laser beam is coupled between the porous metal pad and the body at a plurality of locations, so as to form a coalescence of metal between the porous metal pad and the body.

An advantage of the present invention is that the porous metal pad is attached to the orthopaedic implant body without using the relatively slow process of diffusion bonding or sintering.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
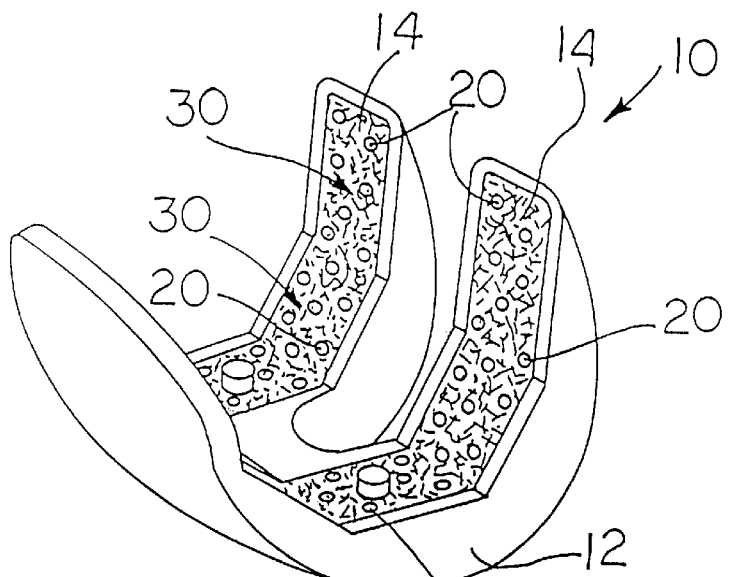
FIG. 1 is a perspective view of an embodiment of a femoral knee component manufactured using the method of the present invention.
Figure 2:
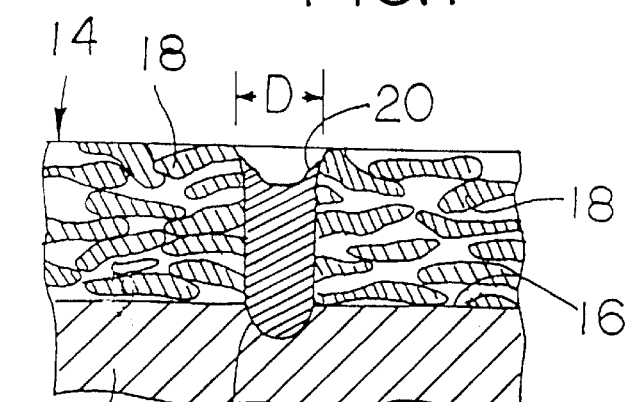
FIG. 2 is an enlarged, fragmentary view showing interconnection between a porous metal pad and a body of an orthopaedic implant using the method of the present invention.

Referring now to the drawings, and more particularly to FIGS. 1 and 2, there is shown an embodiment of an orthopaedic implant manufactured using the method of the present invention. In the embodiment shown, the orthopaedic implant is in the form of a femoral knee component 10, including an orthopaedic implant body 12 and a porous metal pad 14.

Body 12 includes a plurality of adjoining, generally planar supporting surfaces for supporting and attachment with porous metal pad 14, one of which is shown and referenced 16 in FIG. 2. Body 12 is formed from a material such as cobalt-chromium alloy, titanium alloy or stainless steel alloy.

Porous metal pad 14 is placed against supporting surface 16 of body 12, and attached thereto in a manner as will be described hereinafter. Porous metal pad 14, in the embodiment shown, is in the form of a fiber metal pad 14 having a plurality of metal fibers 18 which are interconnected together in a known manner, such as by using a sintering or diffusion bonding process. Fiber metal pad 14 is preferably formed from a material such as cobalt-chromium alloy, titanium alloy or stainless steel alloy.

Fiber metal pad 14 is attached to body 12 by coupling a laser beam (not shown) between fiber metal pad 14 and body 12, so as to form a coalescence of metal between fiber metal pad 14 and body 12. The process of "coupling" using a laser means that enough energy is transferred into the material to melt the material. An example of a laser which may be utilized with the present invention is a YAG industrial laser manufactured by Lumonics Corporation, Livonia, Mich., USA, although many other types of commercially available lasers can also be used with the method of the present invention. More particularly, the laser beam is coupled between fiber metal pad 14 and body 12 at a plurality of locations indicated generally by reference numbers 20. As the laser is coupled between fiber metal pad 14 and body 12, a portion of fiber metals 18 and body 12 melt to define a weld bead which interconnects fiber metal pad 14 and body 12 upon cooling. The weld bead may be in the form of a substantially cylindrical layer 22 which extends through fiber metal pad 14 and into body 12. Cylindrical layer 22 has a diameter which corresponds to a diameter of the laser beam. In the embodiment shown in the drawings, cylindrical layer 22 has an outside diameter "D" of between approximately 0.020 and 0.050 inch and preferably approximately 0.30 inch.

Although the weld bead produced by the coalescing of material between fiber metal pad 14 and body 12 is shown as a substantially cylindrical layer 22 in FIG. 2, it is also to be understood that the weld bead may be in the form of a cone, solid bead or other shape. The shape of the weld bead is primarily dependent upon the density of metal fibers 18 which the laser beam contacts.

The laser utilized with the present invention is adjusted so that the power and beam diameter correspond to the particular type of porous metal pad 14 which is used. For example, a cobalt-chromium-molybdenum fiber metal pad 14 may be placed in a light box in such a way as to allow light passing through the pores of the fiber metal pad 14 to be detected by a video camera. Digitized images of the pores in the fiber metal pad may be captured with a computer assisted image analysis system. The size distribution of the through pores in the fiber metal pad may be used to estimate a minimum laser beam diameter which is required for the production of quality weldments. The laser beam diameter may be adjusted, e.g., by changing the angle of the reflective mirror in the laser. A laser beam diameter of between approximately 0.015 and 0.030 inch has been found effective to produce a weld diameter of between approximately 0.020 and 0.050 inch.

The phrase "laser beam welding", or other derivative spellings thereof, as used in this application, is intended to mean welding using a high energy source, such as laser beam welding, electron beam welding, plasma welding, etc.

Figure 6:
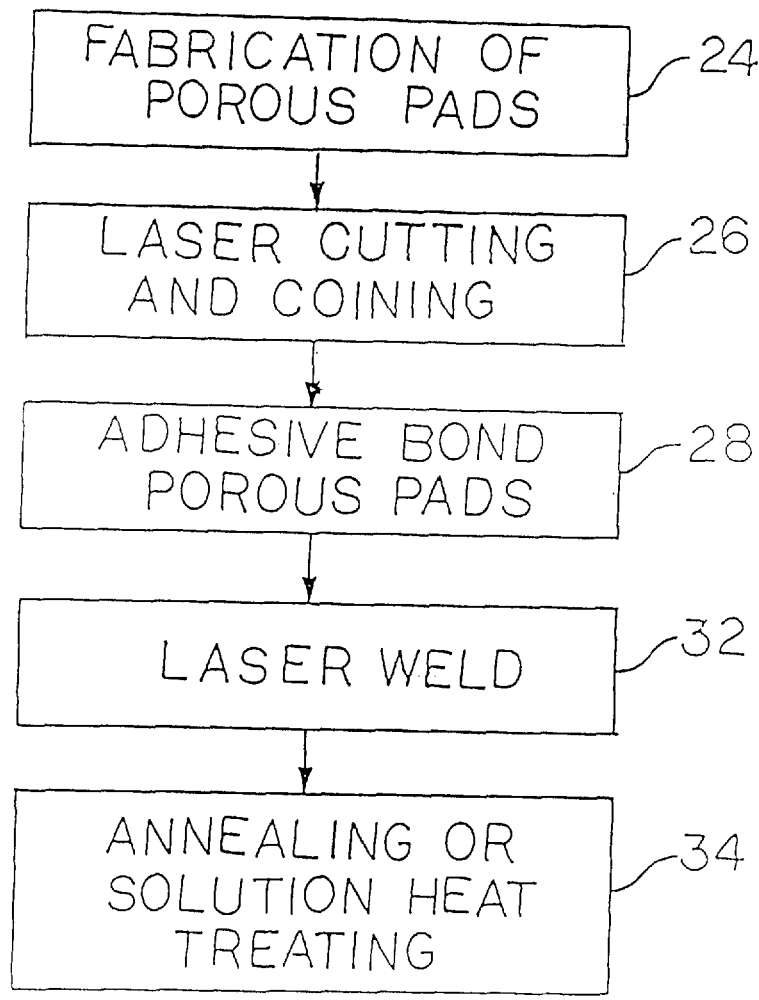
FIG. 6 is a flowchart illustrating an embodiment of the method of the present invention.

Referring now to FIG. 6, there is shown a flow chart illustrating an embodiment of the method of the present invention. First, a porous pad or fiber metal pad 14 is formed or fabricated in known manner using a sintering or diffusion bonding process (block 24). The fiber metal pad is then laser cut into a shape which mates with supporting surface 16 of body 12 (block 26). The fiber metal pad may be formed as a continuous piece which extends from one supporting surface to another. The fiber metal pad may also be coined if desired (block 26). Thereafter, fiber metal pad 14 is attached to supporting surface 16 of body 12 using an adhesive (block 28). Alternatively, fiber metal pad 14 may be clamped against supporting surfaces 16, as indicated schematically by arrows 30 in FIG. 1. After fiber metal pad 14 is adhesively bonded or clamped to body 12, a laser beam is coupled between fiber metal pad 14 and body 12 at a plurality of locations 20 (block 32). The mixture of melted and subsequently cooled metal of fiber metal pad 14 and body 12 welds fiber metal pad 14 to body 12. The orthopaedic implant is then annealed or solution heat treated (block 34), and the previously applied adhesive removed.

Figure 3:
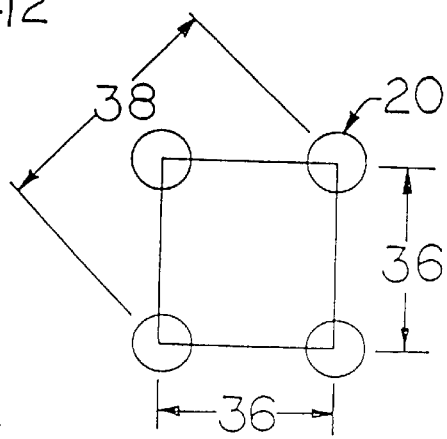
FIGS. 3–5 illustrate different embodiments of patterns at which the porous metal pad is laser welded to the implant body.
Figure 4:
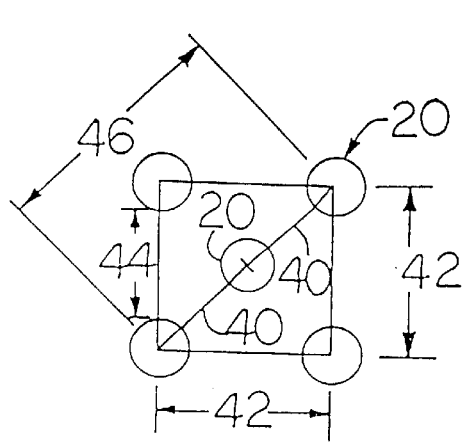
Figure 5:
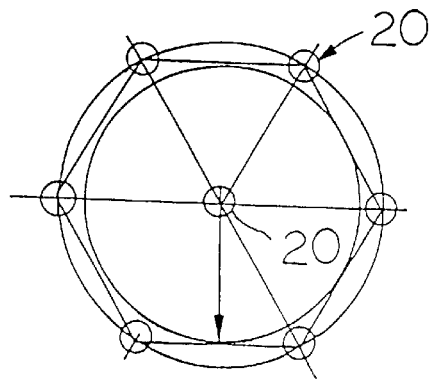

As indicated above, the laser beam is coupled between fiber metal pad 14 and body 12 at a plurality of locations. The plurality of weldment locations 20 may correspond to a predetermined pattern or a random pattern. Laser weldment locations 20 preferably have a spacing therebetween of approximately 0.040 and 0.150 inch, and more preferably a spacing of approximately 0.070 inch. Referring to FIGS. 3–5, three different possible patterns of laser weldment locations are shown. FIG. 3 illustrates a plurality of weldment locations which define a substantially square pattern. Each laser weld location 20 has a diameter D (FIG. 2) of between 0.10 and 0.60 inch, and preferably approximately 0.40 inch. Dimensions between adjacent laser weld locations 20, indicated by reference number 36, are approximately 0.80 inch; and the dimension from corner to corner, indicated by reference number 38, is approximately 0.113 inch.

FIG. 4 illustrates a plurality of weldment locations 20 defining a substantially square pattern with a centrally positioned welding location 20 therein. Each weldment location 20 preferably has a diameter D of approximately 0.40 inch. Dimensions 40 are approximately 0.031 inch; dimensions 42 are approximately 0.100 inch; dimension 44 is approximately 0.060 inch; and dimension 46 is approximately 0.141 inch.

FIG. 5 illustrates a plurality of weldment locations 20 which define a substantially hexagonal pattern, including a centrally located weldment location 20.

In the embodiment shown, orthopaedic implant 10 is in the form of a femoral knee component. However, it is also to be understood that the method of the present invention may be used with other orthopaedic implants, such as a hip, shoulder, elbow or ankle implant, or a permanently implanted fixation rod.

Moreover, in the embodiment shown, porous metal pad 14 is in the form of a fiber metal pad. However, it is also to be understood that other types of porous metal pads such as a beaded pad or wire mesh may also be utilized with the method of the present invention.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of making an orthopaedic implant, comprising the steps of:

forming an orthopaedic implant body, said body including a supporting surface;

placing a porous metal pad against said supporting surface of said body; and coupling a laser beam between said porous metal pad and said body to form a coalescence of metal between said porous metal pad and said body.

2. The method of claim 1, wherein said coalesced metal defines a weld bead which interconnects said porous metal pad with said body.

3. The method of claim 2, wherein said weld bead defines a substantially cylindrical layer, said cylindrical layer having a diameter corresponding to a diameter of said laser beam.

4. The method of claim 3, wherein said cylindrical layer has an outside diameter of approximately 0.30 inch.

5. The method of claim 1, wherein said coupling step comprises coupling said laser beam between said porous metal pad and said body at one of a plurality of locations, and further comprising the repeated step of coupling said laser beam between said porous metal pad and said body at a remainder of said plurality of locations.

6. The method of claim 5, wherein said plurality of locations define a substantially square pattern.

7. The method of claim 6, wherein said square pattern includes a centrally positioned welding location.

8. The method of claim 5, wherein said plurality of locations define a substantially hexagonal pattern.

9. The method of claim 8, wherein said hexagonal pattern includes a centrally positioned welding location.

10. The method of claim 5, wherein said plurality of locations have a spacing therebetween of between approximately 0.040 and 0.150 inch.

11. The method of claim 10, wherein said plurality of locations have a spacing therebetween of approximately 0.070 inch.

12. The method of claim 1, wherein said supporting surface comprises a plurality of adjoining supporting surfaces, and wherein said placing step comprises placing said porous metal pad against each of said supporting surfaces.

13. The method of claim 1, comprising the further step of clamping said porous metal pad against said supporting surface, said clamping step occurring between said placing step and said coupling steps.

14. The method of claim 1, comprising the further step of adhesively bonding said porous metal pad to said supporting surface.

15. The method of claim 1, comprising the further step of cutting said porous metal pad to fit said supporting surface, said cutting step occurring prior to said placing step.

16. The method of claim 1, wherein said porous metal pad comprises one of interconnected metal fibers, metal beads and a metal mesh.

17. The method of claim 1, wherein said fiber metal pad is comprised of a material selected from the group consisting of a cobalt-chromium alloy, titanium alloy and stainless steel alloy.

18. The method of claim 1, wherein said implant body is comprised of a material selected from the group consisting of a cobalt-chromium alloy, titanium alloy and stainless steel alloy.

19. The method of claim 14, comprising the further step of annealing the implant to remove adhesive used in the adhesively bonding step, the annealing step following the coalescence step.

20. A method of making an orthopaedic implant, comprising the steps of:

forming an orthopaedic implant body, said body including a supporting surface;

forming a porous metal pad to fit said supporting surface; at least one of clamping and adhesively bonding said porous metal pad to said supporting surface; and coupling a laser beam between said porous metal pad and said body to form a coalescence of metal between said porous metal pad and said body.

21. The method of claim 20, wherein said coalesced metal defines a weld bead which interconnects said porous metal pad with said body.

22. The method of claim 21, wherein said weld bead defines a substantially cylindrical layer, said cylindrical layer having a diameter corresponding to a diameter of said laser beam.

23. The method of claim 20, wherein said coupling step comprises coupling said laser beam between said porous metal pad and said body at one of a plurality of locations, and further comprising the repeated step of coupling said laser beam between said porous metal pad and said body at a remainder of said plurality of locations.

24. A method of making an orthopaedic implant, comprising the steps of:

forming an orthopaedic implant body, said body including a supporting surface;

forming a porous metal pad to fit said supporting surface;

at least one of clamping and adhesively bonding said porous metal pad to said supporting surface; and coupling a laser beam between said porous metal pad and said body to form a coalescence of metal at a plurality of locations between said porous metal pad and said body;

wherein said coalesced metal are formed by weld beads which interconnects said porous metal pad with said body;

wherein a portion of said weld beads defines a substantially cylindrical layer, said cylindrical layer having a diameter corresponding to a diameter of said laser beam.

* * * * *